(12) United States Patent
Walmsley et al.

(10) Patent No.: US 10,016,127 B2
(45) Date of Patent: Jul. 10, 2018

(54) OPHTHALMIC DEVICE, METHOD AND SYSTEM

(71) Applicant: INGENEUS PTY LTD, Victoria (AU)

(72) Inventors: Richard Gordon Walmsley, Victoria (AU); David James Lockwood, Victoria (AU); Michael Andrew Coote, Victoria (AU)

(73) Assignee: INGENEUS PTY LTD, Victoria (AU)

( * ) Notice: Subject to any disclaimer, the term of this patent is extended or adjusted under 35 U.S.C. 154(b) by 0 days.

(21) Appl. No.: 15/120,337

(22) PCT Filed: Feb. 20, 2015

(86) PCT No.: PCT/AU2015/000091
§ 371 (c)(1),
(2) Date: Aug. 19, 2016

(87) PCT Pub. No.: WO2015/123724
PCT Pub. Date: Aug. 27, 2015

(65) Prior Publication Data
US 2017/0065167 A1     Mar. 9, 2017

(30) Foreign Application Priority Data
Feb. 20, 2014   (AU) ................................ 2014900549

(51) Int. Cl.
*A61B 3/10*          (2006.01)
*A61B 3/032*         (2006.01)
(Continued)

(52) U.S. Cl.
CPC ............... *A61B 3/032* (2013.01); *A61B 3/00* (2013.01); *A61B 3/0008* (2013.01);
(Continued)

(58) Field of Classification Search
CPC ... A61B 3/13; A61B 2090/309; A61B 3/0008; A61B 3/103; A61B 3/18; A61B 5/742; A61B 3/135
(Continued)

(56) References Cited
U.S. PATENT DOCUMENTS 5,576,780 A    11/1996  Yancey
5,848,175 A    12/1998  Akashi
(Continued)

OTHER PUBLICATIONS

International Search Report dated Jan. 30, 2015 for corresponding application No. AU 2014900549.
(Continued)

*Primary Examiner* — Hung Dang
(74) *Attorney, Agent, or Firm* — Renner Otto Boisselle and Sklar

(57) ABSTRACT

The present invention relates to an eye testing and image capture device for testing and examination of an eye comprising an image display device to display an image for viewing by an eye to be tested; an image capture device to capture an image of the eye; a beam splitter positioned to split light between the image capture device and the image display device; and a lighting array for illuminating the eye wherein the lighting array comprises a first array positioned at a first angle to the eye and a second array positioned at a second angle to the eye and the first array and second array comprise two or more different light types. The present invention also relates to a method of obtaining eye test data and one or more image of an eye as well as to a system and method of screening a patient using the device and method.

20 Claims, 12 Drawing Sheets

(51) Int. Cl.
*A61B 3/00* (2006.01)
*A61B 3/14* (2006.01)
*G02B 27/10* (2006.01)
*G06T 5/00* (2006.01)
*G06T 5/50* (2006.01)
*H04N 5/225* (2006.01)
*H04N 5/232* (2006.01)
*H04N 5/235* (2006.01)
*H04N 5/262* (2006.01)
*H04N 7/18* (2006.01)

(52) U.S. Cl.
CPC .......... *A61B 3/0025* (2013.01); *A61B 3/0033* (2013.01); *A61B 3/14* (2013.01); *G02B 27/10* (2013.01); *G06T 5/009* (2013.01); *G06T 5/50* (2013.01); *H04N 5/2254* (2013.01); *H04N 5/2256* (2013.01); *H04N 5/2354* (2013.01); *H04N 5/23293* (2013.01); *H04N 5/2625* (2013.01); *H04N 7/183* (2013.01); *G06T 2207/20221* (2013.01)

(58) Field of Classification Search
USPC ........ 351/211, 214, 221, 246, 237, 239, 243
See application file for complete search history.

(56) References Cited

U.S. PATENT DOCUMENTS

| | | | |
|---|---|---|---|
| 5,993,001 | A | 11/1999 | Bursell et al. |
| 6,193,371 | B1 | 2/2001 | Snook |
| 7,625,087 | B2 | 12/2009 | Taylor et al. |
| 2002/0052551 | A1 | 5/2002 | Sinclair et al. |
| 2002/0060778 | A1* | 5/2002 | Su .................. A61F 9/008 351/206 |
| 2005/0203422 | A1 | 9/2005 | Wei |
| 2006/0177205 | A1 | 8/2006 | Steinkamp |
| 2007/0031002 | A1 | 2/2007 | Venkatesh et al. |
| 2008/0165322 | A1 | 7/2008 | Su et al. |
| 2010/0097573 | A1 | 4/2010 | Verdooner et al. |

OTHER PUBLICATIONS

Written Opinion dated Apr. 1, 2015 for corresponding application No. PCT/AU2015/000091.
International Search Report dated Apr. 1, 2015 for corresponding application No. PCT/AU2015/000091.

* cited by examiner

OPHTHALMIC DEVICE, METHOD AND SYSTEM

This application is a national phase of International Application No. PCT/AU2015/000091 filed Feb. 20, 2015 and published in the English language.

FIELD OF THE INVENTION

The present invention relates to an ophthalmic device, method and system. More particularly, this invention relates to an ophthalmic device, method and system for obtaining an image of the eye and ophthalmic data suitable for communication through a network.

BACKGROUND TO THE INVENTION

In Australia, and many other countries, rural and remote areas suffer from a lack of ophthalmic service coverage.

The number of eye injuries, while serious in outcome, makes up only a small percentage of Emergency Department presentations. Therefore resourcing Emergency Departments for this type of specialty is difficult and not cost effective.

Ophthalmology is one of the more expensive specialties in which to set up a practice due to the cost of equipment and devices. Additionally, the equipment used by ophthalmologists for diagnosis is complex and difficult to use. Although trainee doctors are given some exposure to this complex equipment, typically the training is brief and quickly forgotten. Moreover, few ophthalmologists are available to Emergency Departments or to public patients.

Clinically, the eye is something that clinicians from non-ophthalmic backgrounds are reticent to work on. This is because eyes are perceived as sensitive and easily disturbed.

Further complicating the treatment of ophthalmic patients is that, from a patient perspective, the pain of an eye injury may not be directly related to the seriousness of the underlying issue. This adds to both the complexity of any diagnosis and treatment.

SUMMARY OF THE INVENTION

The present invention is broadly directed to a method and device for obtaining ophthalmic data that may be used to make an assessment of an eye disease, injury or condition or suspected eye disease, injury or condition remotely.

In another broad form, the invention relates to a device for capturing one or more image of an eye and performing one or more assessment of the eye. The captured image and assessment may be communicated to a remote location by a network to allow remote assessment of the eye. The captured image may be obtained by a user operating the device locally or remotely. A preferred advantage of the device, method and system of the present invention is that the device is easy to use and the system and method make efficient use of ophthalmological expertise.

In a first aspect, the invention provides an eye testing and image capture device for testing and examination of an eye comprising:
 an image display device to display an image for viewing by an eye to be tested;
 an image capture device to capture an image of the eye to be examined;
 a beam splitter positioned to split light between the image capture device and the image display device; and
 a lighting array for illuminating the eye to be tested and imaged wherein the lighting array comprises a first array positioned at a first angle to the eye and a second array positioned at a second angle to the eye and the first array and second array comprise two or more different light types.

In one embodiment of the first aspect, the displayed image is viewed by or visible to the eye simultaneously with the captured image being captured.

According to another embodiment of the first aspect, the two or more light types comprise white light and light of a defined wavelength.

In one embodiment of the first aspect, the two or more light types may comprise a slit light source.

According to another embodiment of the first aspect, the light of a defined wavelength may comprise coloured light. The coloured light may comprise or may be blue light.

In yet another embodiment of the first aspect, the light types comprise a blue light source, a white light source and a slit light source.

According to another embodiment of the first aspect, the intensity of the illuminated light from any one of the light sources may be varied independently. When the light source comprises an LED, the intensity may be varied by varying the current.

According to one embodiment of the first aspect, each of the two or more different light types comprises respective lower light sources and upper light sources which may be individually complementarily illuminated in a series of captured images so that a light artefact may be eliminated or at least substantially reduced.

According to one embodiment of the first aspect, the complementarily illuminated light sources comprise the complementary pairs of a lower light source in the first array and an upper light source in the second array or an upper light source in the first array and a lower light source in the second array.

According to one embodiment of the first aspect, each of the two or more different light types may be illuminated independently.

The blue light source may comprise one or more blue LEDs and the white light source may comprise one or more white LEDs.

The one or more blue LEDs may comprise one or more lower blue LEDs and one or more upper blue LEDs.

The one or more white LEDs may comprise one or more lower white LEDs and one or more upper white LEDs.

The one or more blue LEDs may comprise two or more blue LEDs in parallel alignment.

The one or more white LEDs may comprise two or more white LEDs in parallel alignment.

In one embodiment of the first aspect the complementary pairs of light sources are operable to illuminate the eye in a series of captured images such that a light artefact occurs at a different location in different images in the series.

According to another embodiment of the first aspect, the first array and the second array may be diagonally opposed.

The device of the first aspect may further comprise an image capture device to capture the series of images.

The device of the first aspect may further comprise an image processor to process the series of images to produce a composite image with elimination or substantial elimination of the light artefact.

According to another embodiment of the first aspect, the device further comprises a preview screen. The preview screen may be comprised on a display wirelessly connected to the device.

According to yet another embodiment of the first aspect, the device further comprises a controller for controlling the image displayed in the image display device and/or controlling the capture of images by the image capture device.

The controller may also control the illumination of the lighting array.

According to another embodiment of the first aspect, the image display device may display one or more visual function testing stimuli.

The visual function testing stimuli may comprise one or more of a visual acuity test, a field test, a distortion test, a colour vision test, a contrast sensitivity test and/or a flicker fusion test. The distortion test may comprise an Amsler grid.

The image capture device may comprise one or more CMOS or CCD sensor array.

According to one embodiment of the first aspect, the device further comprises a mirror disposed between the beam splitter and one or more of the image capture device and the image display device.

According to another embodiment of the first aspect, the device also comprises one or more lens. The one or more lens may be located between the eye and the beam splitter; between the beam splitter and the image capture device; and/or between the beam splitter and the image display device.

According to yet another embodiment of the first aspect, the device further comprises one or more input for entering operator details, patient data and/or eye test response data.

According to still another embodiment of the first aspect, the device is connected to a network for communication of ophthalmic screening data to a remote location and optionally for receiving a determination based on a review of the ophthalmic screening data at the remote location.

The ophthalmic screening data may comprise one or more captured image and optionally one or more of operator details; patient data and eye test response data.

In another embodiment of the first aspect, the image processor may also process the series of images or the composite image using an algorithm to detect a disease or condition requiring referral and/or treatment.

In embodiments of the first aspect wherein a disease or condition requiring referral and/or treatment is detected, the device may connect to a remote computer at which the referral and/or treatment may be performed.

According to another embodiment of the first aspect, the device comprises a surgical or therapeutic apparatus that is controlled through the network by a user on a remote computer.

In one embodiment, the surgical or therapeutic apparatus comprises a laser that may be controlled by a user using a remote computer to apply laser light to the eye. Preferably, the surgical or therapeutic apparatus is one that does not make physical contact with the eye.

In a second aspect, the invention provides a method of obtaining eye test data and one or more image of an eye, the method comprising:

illuminating the eye to be tested and imaged with an illumination device comprising a first lighting array positioned at a first angle to the eye and a second lighting array positioned at a second angle to the eye wherein the first lighting array and second lighting array comprise two or more different light types;

displaying an image for viewing by the eye on an image display device;

capturing an image of the eye with an image capture device; and splitting light between the image capture device and the image display device wherein the displayed image is viewed by the eye simultaneously with the captured image being captured.

In one embodiment of the second aspect, the method further comprises displaying the image for viewing by the eye simultaneously with the captured image being captured.

According to one embodiment of the second aspect, the two or more light types comprise white light and light of a defined wavelength.

In one embodiment of the second aspect, the two or more light types may further comprise a slit light source.

In another embodiment of the second aspect, the light types comprise a blue light source, a white light source and a slit light source.

The light of a defined wavelength may comprise coloured light. The coloured light may comprise or may be blue light.

According to one embodiment of the second aspect, each of the two or more different light types may be illuminated independently.

According to another embodiment of the first aspect, the intensity of the illuminated light from any one of the light sources may be varied independently. When the light source comprises an LED, the intensity may be varied by varying the current.

According to one embodiment of the second aspect, each of the two or more different light types comprise respective lower light sources and upper light sources which may be individually complementarily illuminated in a series of captured images so that a light artefact may be eliminated or at least substantially reduced.

According to another embodiment of the second aspect, the complementarily illuminated light sources comprise the complementary pairs of a lower light source in the first array and an upper light source in the second array or an upper light source in the first array and a lower light source in the second array.

When a series of images is captured the method may further comprise viewing two or more images in the series to view the entirety of the object.

In another embodiment of the second aspect, the method further comprises processing the series of images to produce a composite image that does not comprise or does not substantially comprise a light artefact.

The blue light source may comprise one or more blue LEDs and the white light source may comprise one or more white LEDs.

The one or more blue LEDs may comprise one or more lower blue LEDs and one or more upper blue LEDs.

The one or more white LEDs may comprise one or more lower white LEDs and one or more upper white LEDs.

The one or more blue LEDs may comprise two or more blue LEDs in parallel alignment.

The one or more white LEDs may comprise two or more white LEDs in parallel alignment.

In one embodiment of the second aspect the complementary pairs of light sources illuminate the eye in a series of captured images such that a light artefact occurs at a different location in different images in the series.

In another embodiment of the second aspect, the complementary pair of light sources comprise a lower light source in the first array and an upper light source in the second array or an upper light source in the first array and a lower light source in the second array.

According to another embodiment of the second aspect, the first array and second array may be diagonally opposed.

Each of the two or more different light types may comprise respective lower light sources and upper light sources which individually may be complementarily illuminated in the different images in the series.

The method of the first aspect may further comprise capturing the series of images with an image capture device.

The method of the second aspect may further comprise processing the series of images with an image processor to produce a composite image with elimination or substantial elimination of the light artefact.

In one embodiment of the second aspect, the method further comprises displaying a preview screen displaying a digital image generated by the image capture device. The preview screen may be comprised on a display wirelessly connected to the device.

According to another embodiment of the second aspect, the method further comprises controlling with a controller the image displayed in the image display device and/or the capture of images by the image capture device.

According to another embodiment of the second aspect, the method further comprises controlling with the controller the illumination of the lighting array.

According to yet another embodiment of the second aspect, the method further comprises displaying one or more visual function testing stimuli on the image display device.

The visual function testing stimuli may comprise one or more of a visual acuity test, a field test, a distortion test, a colour vision test, a contrast sensitivity test and/or a flicker fusion test. The distortion test may comprise an Amsler grid.

According to still another embodiment of the second aspect, the method further comprises inputting one or more of operator details, patient data and/or eye test response data.

According to another embodiment of the second aspect, the method further comprises communicating ophthalmic screening data to a remote location via a network and optionally receiving a determination based on review of the ophthalmic screening data at the remote location via the network.

In another embodiment of the second aspect, the method further comprises processing the series of images or the composite image using an algorithm to detect a disease or condition requiring referral and/or treatment.

In embodiments of the second aspect wherein a disease or condition requiring referral and/or treatment is detected, the method may further comprise connecting to a remote computer at which the referral and/or treatment may be performed.

According to another embodiment of the second aspect, the method comprises a user controlling a surgical or therapeutic apparatus that is housed on the device with a remote computer through a network.

In yet another embodiment of the second aspect, the surgical or therapeutic apparatus comprises a laser that may be controlled using a remote computer to apply laser light to the eye.

In an third aspect the invention provides a system for screening a patient, the system comprising:
  an input into which eye test response data and optionally operator details and/or patient data is entered, the input comprising eye test information;
  an image capture device to capture one or more image of an eye of the patient, the captured one or more image comprise eye image information;
  a computer for providing the obtained eye test information and eye image information to a remote computer via a network;
  the remote computer for reviewing the obtained eye test information and eye image information at a location remote to the computer and for entering a determination of a next course of action based on the review;
  receiving on the computer the determined next course of action through the network.

In one embodiment of the third aspect, the image capture device comprises the device of the first aspect.

According to another embodiment of the third aspect, the system further comprises communicating ophthalmic screening data to a remote location via a network and optionally receiving a determination based on review of the ophthalmic screening data at the remote location via the network.

In a fourth aspect the invention provides a method for screening a patient, the method comprising:
  inputting eye test response data and optionally operator details and/or patient data into a computer, the input data comprising eye test information;
  capturing with an image capture device one or more image of an eye of the patient the captured one or more image comprising eye image information;
  providing with a computer the obtained eye test information and eye image information to a remote computer via a network;
  displaying on a remote computer the obtained eye test information and eye image information at a location remote to the computer for review;
  entering a determination of a next course of action based on the review into the remote computer; and
  receiving on the computer the determined next course of action through the network.

In one embodiment of the fourth aspect, the inputting and/or capturing is performed by the method of the second aspect.

In a fifth aspect the invention provides a positioning device comprising:
  a head receiving section spaced from and disposed at an angle to a base;
  one or more x-axis adjustment arm along which an attached device may move to change the position of the attached device relative to the head receiving section;
  one or more y-axis adjustment arm along which the attached device may move to change the position of the attached device relative to head receiving section; and
  one or more z-axis adjustment arm along which an attached device may move to change the position of the attached device relative to the head receiving section.

In one embodiment of the fifth aspect, the attached device comprises the eye testing and image capture device of the first aspect or the system for screening a patient of the third aspect.

In another embodiment of the fifth aspect the positioning device is motorized to drive movement along one or more axes. In the motorized embodiment, the attached device may be positioned in response to user command.

In yet another embodiment of the fifth aspect, the head receiving section is disposed at an angle between 5 and 35 degrees; 10 and 30 degree; 15 and 25 degrees; or at 20 degrees.

In still another embodiment of the fifth aspect, one or more of the adjustment arms comprise fine and course adjustment.

In a sixth aspect the invention provides an image or a series of images captured by the device of the first aspect or the system of the third aspect.

In a seventh aspect the invention provides an image or a series of images captured by the method of the second aspect or fourth aspect.

Where the terms "comprise", comprises", "comprising", "include", "includes", "included" or "including" are used in this specification, they are to be interpreted as specifying the presence of the stated features, integers, steps or components referred to, but not to preclude the presence or addition of one or more other feature, integer, step, component or group thereof.

Further, any prior art reference or statement provided in the specification is not to be taken as an admission that such art constitutes, or is to be understood as constituting, part of the common general knowledge.

BRIEF DESCRIPTION OF THE FIGURES

In order that the present invention may be readily understood and put into practical effect, reference will now be made to the accompanying illustrations, wherein like reference numerals refer to like features and wherein.

DETAILED DESCRIPTION OF THE INVENTION

The following description refers to specific embodiments of the present invention and is in no way intended to limit the scope of the present invention to those specific embodiments.

Figure 1A:
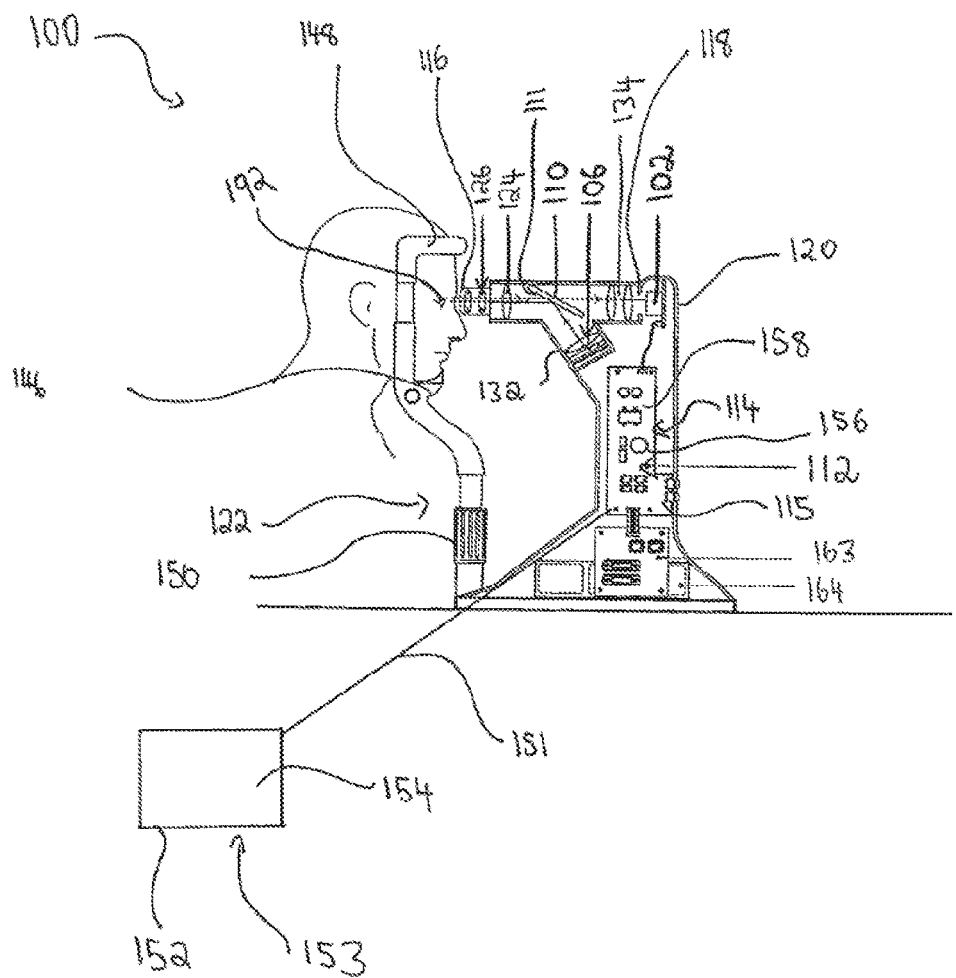
FIG. 1A: shows a schematic diagram showing a side view of one embodiment of a device eye testing and image capture device according to one embodiment of the invention.

One embodiment of an eye testing and image capture device 100 is shown in FIG. 1A. Device 100 is shown to comprise a beam splitter 110 positioned between a viewing window 116 on one side and an image display device 106 and an image capture device 102 on the other side of beam splitter 110.

Image display device 106 comprises a Liquid-Crystal Display (LCD) for presenting a displayed image 104 (not shown) for viewing by eye 192. In other embodiments, image display device 106 may comprise other suitable displays, for example, an organic light-emitting diode (OLED) or a projector. From the teaching herein a skilled person is readily able to select other suitable display devices 106.

Displayed image 104 may comprise visual function testing stimuli for example, a visual acuity test, a field test, a distortion test, a colour vision test, a contrast sensitivity test and/or a flicker fusion test. The visual acuity test may comprise a random optotype or one or more series of optotypes or a chart such as, a logMAR chart, a Snellen chart, a Landolt C chart, a Lea test and a Jaeger chart. The acuity test may comprise optotypes such as, a letter of the alphabet, a number, geometric symbol, a simple picture or symbol. The distortion test may comprise an Amsler grid. A skilled person is readily able to select other suitable displayed images 104.

The displayed image 104 is a high resolution image that is amplified and projected with display lens 132.

Displayed image 104 may be projected with infinity focus. The infinity focus is achieved by display lens 132. In the embodiment shown in FIG. 1A, display lens 132 comprises a single lens. In other embodiments, lens 132 comprises a series of two or more lenses.

Image capture device 102 comprises a DFK72AUC02-F high resolution colour camera for obtaining high resolution digital images of eye 192. Device 102 comprises a digital camera comprising a plurality of charge coupled devices (CCDs). From the teaching herein a skilled person readily understands that other image capture devices may be used, including those comprising one or more complementary metal oxide semiconductor (CMOS) sensor or sensor array. From the teaching herein a skilled person is readily able to select other suitable capture devices 102.

Between beam splitter 110 and capture device 102 is located imaging lens series 134. In the embodiment shown in FIG. 1A imaging lens series 134 comprise two lenses. In other embodiments imaging lens series 134 comprises, 1, 3, 4, 5, 6, 7, 8, 9, 10 or more lenses.

Imaging lens series 134 is placed before the capture device 102 to change the size of eye 192 in the captured image 108 (not shown) so that a useful and informative image is captured. Imaging lens series 134 may also be used to control whether captured image 108 comprises a retinal image or an anterior image.

Beam splitter 110 splits the light inside optical cavity 118. The splitting of light by beam splitter 110 ensures that light inside the optical cavity 118 travels so that an image displayed on the image display device 106, the displayed image 104, may be viewed by the eye being tested 192 simultaneously with an image of eye 192 being captured by image capture device 102, the captured image 108.

Beam splitter 110 is positioned so that incident light on beam splitter 110 from display device 106 is transmitted towards eye 192 and incident light from eye 192 is reflected to the capture device 102. In other embodiments beam splitter 110 is positioned so that light from display device 106 is reflected and light from eye 192 is transmitted. It is this splitting of incident light into reflected and transmitted light that enables eye 192 to view displayed image 104 simultaneously with the captured image 108 being obtained by capture device 102.

Figure 7A:
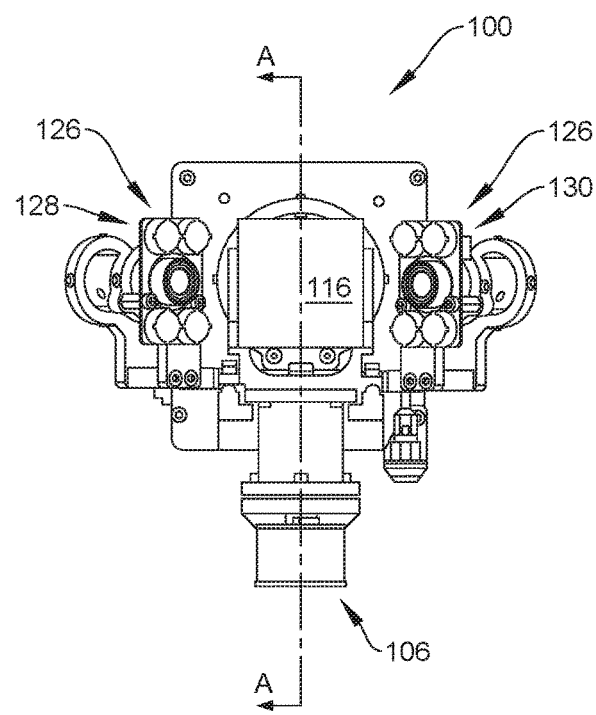
FIG. 7A: is a front view showing a section A-A.
Figure 7B:
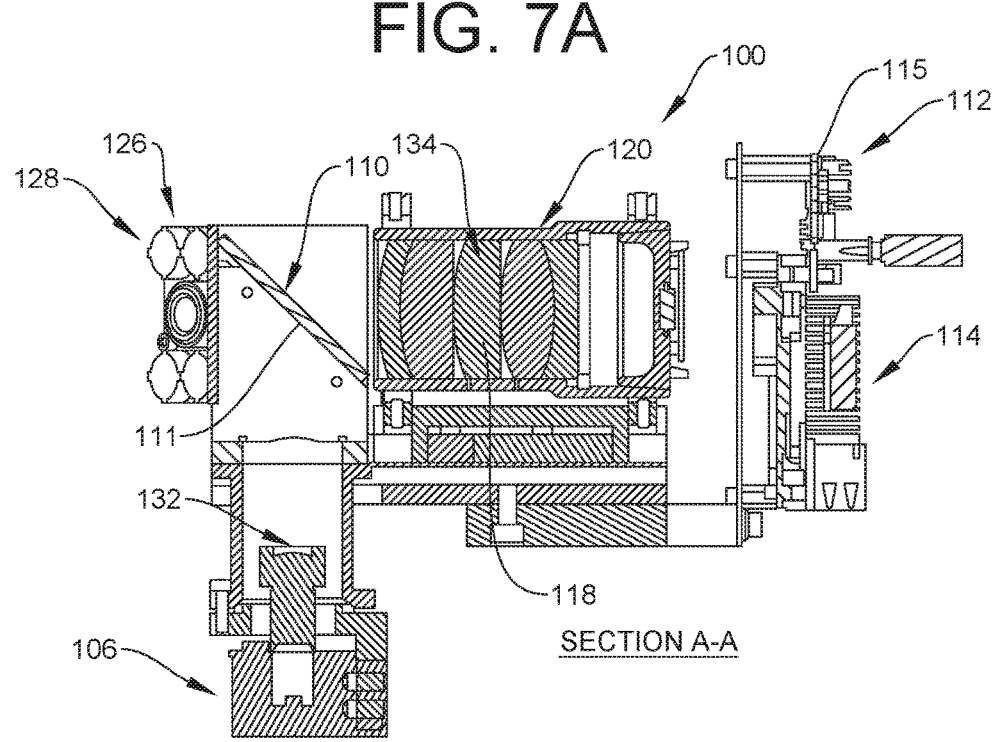
FIG. 7B: is a section view through section A-A shown in FIG. 7A.

As shown in FIG. 7B beam splitter 110 comprises a reflective coating 111 which is partially transmissive to other wavelengths of light to allow vision testing using the display device 106 simultaneously with the capture of a captured image 108.

Beam splitter 110 is a IBX-N-03871-01. From the teachings herein a skilled person is readily able to select a suitable beam splitter and to locate it correctly in device 100.

The device 100 in FIGS. 1B, 2, 4-6 and 7A-7B shows another embodiment of device 100 in which the image display device 106 and the image capture device 102 each comprise separate optical systems that are integrated together by beam splitter 110. That is, in the embodiment of FIGS. 2, 4-6 and 7A-7B, in-between beam splitter 110 and the eye being tested there are no lenses and only flat optics.

Figure 1B:
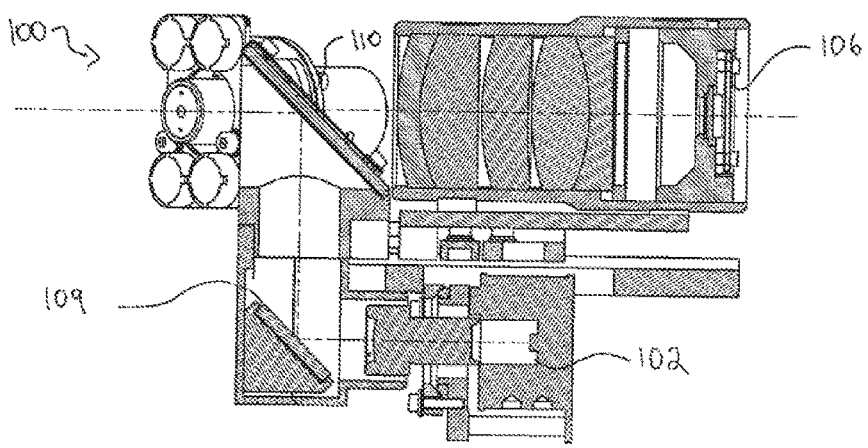
FIG. 1B: shows a schematic diagram showing a side view embodiment of another embodiment of an eye testing and image capture device according to the invention.

FIG. 1B, which shows a cross-section through device 100, shows image display device 106 to be coaxial with the eye 192 to be observed. By adding a mirror 109 after beam splitter 110, image capture device 102 is able to be disposed in the same vertical plane as image display device 106. In the embodiment shown in FIG. 1B image capture device 102 is below image display device 106. In another embodiment, image capture device 102 is above image display device 106.

As the person of skill in the art readily understands if no mirror is used, the camera will record the eye 192 in the correct orientation. If one mirror is used, the camera will record and the displayed image 104 a mirror image. Use of two mirrors will result in the correct orientation for both.

In the first embodiment shown in FIG. 1A, and the second embodiment shown in FIGS. 1B, 2, 4-6 and 7B beam splitter 110 is angled to provide reflected and transmitted light in the appropriate direction. From the teaching herein a skilled person is readily able to select a suitable beam splitter and to position and angle the beam splitter appropriately.

The location of the image display device 106 and image capture device 102 may be interchanged. Depending on their make-up, display lens 132 and imaging lens series 134 may also be required to be interchanged.

In the embodiment of FIG. 1A, an objective lens 124 is positioned between the viewing window 116 and beam splitter 110. Objective lens 124 comprises a single lens, however in other embodiments objective lens 124 may comprise a series of two or more lenses.

Objective lens 124 gathers light from eye 192. When imaging the anterior segment of eye 192, objective lens 124 projects the object to infinity.

As shown in FIGS. 1A, 1B, 2, 4-6 and 7A-B, the optical cavity 118 is defined by housing 120 which encloses the optical components of device 100, namely: the image display device 106; image capture device 102; beam splitter 110; and lenses 124 (FIG. 1A only), 132, 134. Housing 120 also comprises controller 112 which is described below. In the embodiment shown in FIG. 1A, housing 120 is comprised of hard plastic. In other embodiments, casing 120 may be comprised of aluminium or steel.

The eye being tested 192 is positioned, using positioning device 122, to look through viewing window 116 into optical cavity 118. As can be seen in FIGS. 2, 4, 5 and 7A, viewing window 116 is at the front of device 100 and a user looks through it in order to view the image displayed on image display device 116.

Positioning device 122 comprises a chin rest 146, forehead rest 148 and an in-out adjustment 150 that can be swivelled to move positioning device 122 in or away from device 100. Any up-down adjustment may be performed by having patient 190 sit in an adjustable chair such as, for example, a gas-lift chair. From the teaching herein a skilled person is readily able to select or design other suitable patient positioning devices including the other patient positioning devices discussed below.

Also comprised on device 100 is a lighting array 126 for illuminating eye 192. Although general diffuse illumination of eye 192 is provided by ambient lighting, lighting array 126 provides additional illumination which allows capture device 106 to capture specific image types. Lighting array 126 preferably comprises two or more light types such as, white light, light of a defined wavelength and a slit light source.

Figure 2:
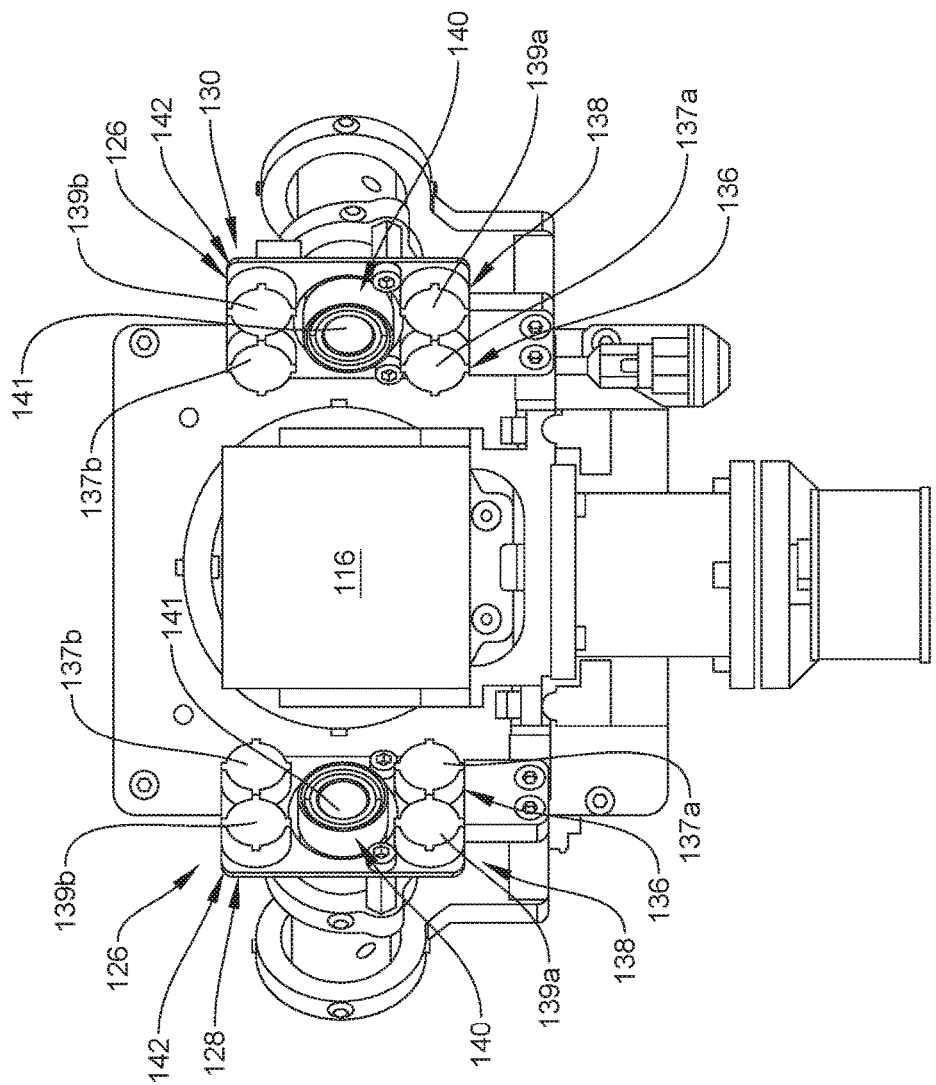
FIG. 2: shows a front view of a device according to one embodiment of the invention.
Figure 5:
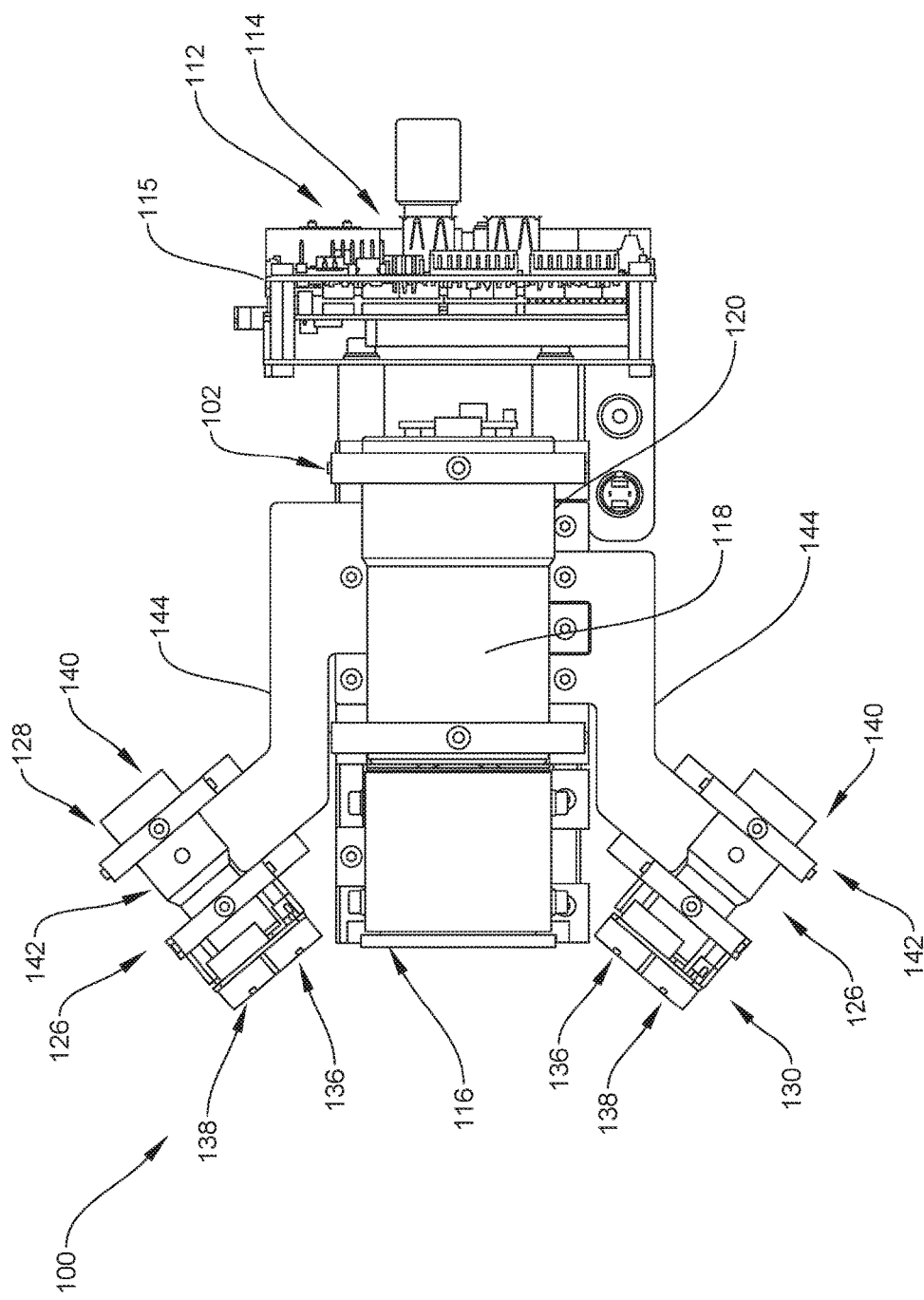
FIG. 5: is a plan view of a device according to one embodiment of the invention.
Figure 6:
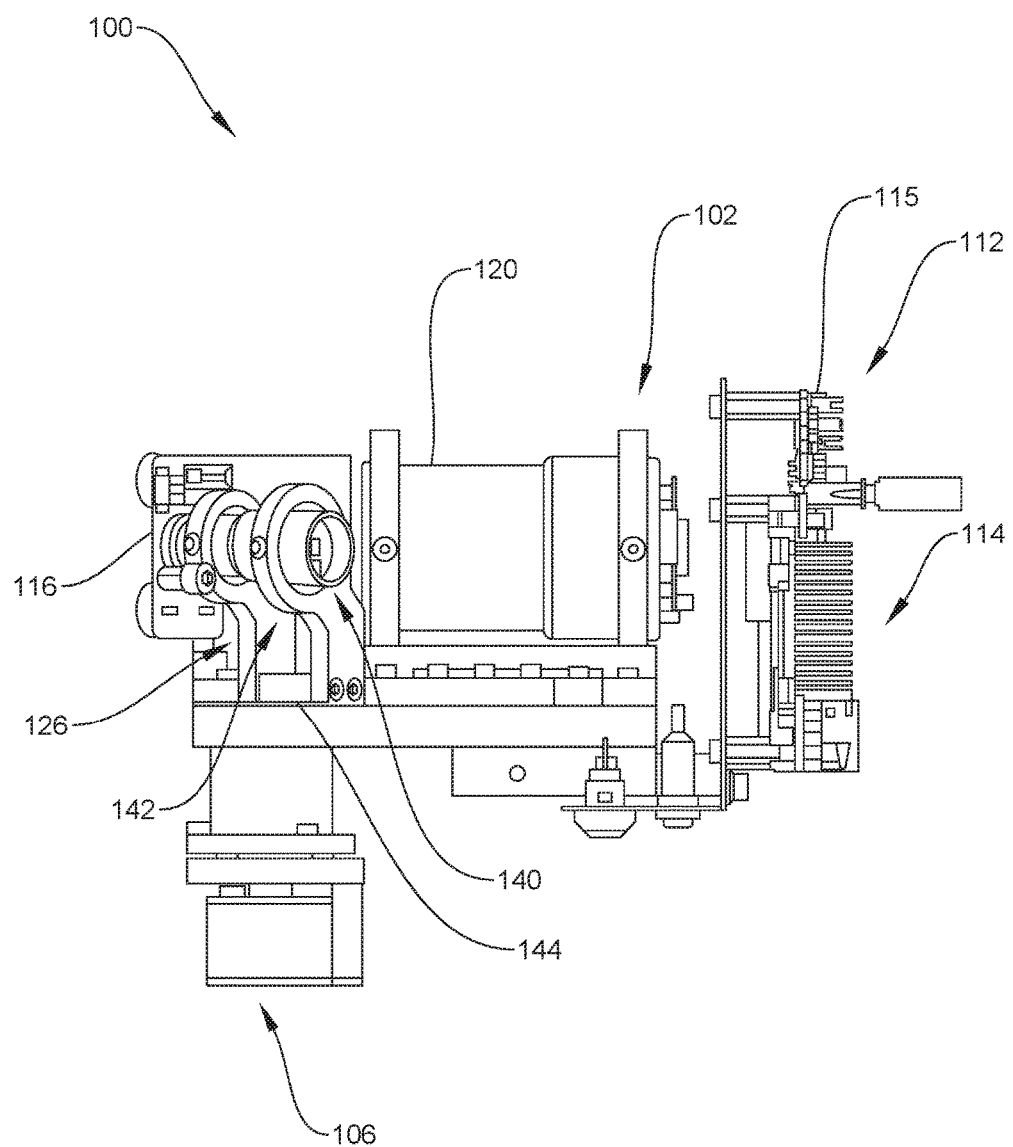
FIG. 6: is a side view of a device according to one embodiment of the invention.

As best shown in FIG. 2, lighting array 126 comprises a first array 128 positioned at a first angle to eye 192 and a second array 130 positioned at a second and different angle to eye 192. Each array is comprised in a respective lighting housing 142. As shown in FIG. 5, this positioning is accomplished by joining arrays 128, 130 to housing 120 by arms 144. In the embodiment shown in FIG. 1, arms 144 are fixed. In other embodiments, arms 144 may be adjustable in position and/or angle to eye 192. The adjustment may be manual or controlled by controller 112.

FIG. 2 also shows both first array 128 and second array 130 to comprise a blue light 136, a white light 138 and a slit light source 140. In the embodiment shown, slit light source 140 comprises a conventional slit lamp. In further embodiments other slit light sources that comprise a high-intensity light source that can be focused to shine a thin sheet of light into the eye can be used.

In the embodiment shown in FIG. 2, slit light source 140 comprises a filter 141. In other embodiments slit light source 140 may comprise one or more filter 141 such as a polariser, diffuser or other filter. The one or more filter 141 may be used to highlight various portions and/or structures of eye 192 in captured image 108. Slit light source 140 may be adjusted to provide a beam of light ranging from a thin slit to a large circular field of light in order to highlight various portions and structures of eye 192.

Blue light 136 comprises two light sources a lower blue LED 137a and an upper blue LED 137b, both of which comprise XPEBLU-L1-B50-M3-0-01 Blue 470-480 nm 45.7 Lumen @350 mA-CUT1130. Similarly, white light 138 comprises the two light sources of a lower white LED 139a and an upper white LED 139b both of which comprise CREE XPG-2 White LEDs 3000-CUT937. The lower LEDs 137a, 139a are located directly below the upper LEDs 137b, 139b. In this arrangement, blue light source 136 comprises two or more blue LEDs 137a, 137b in parallel alignment and white light source 138 comprises two or more parallel white LEDs 139a, 139b in parallel alignment. In other embodiments the lower 137a, 139a and upper LEDs 137b, 139b are not in parallel alignment.

Although blue light 136 and white light 138 comprise two light sources 137a, 137b and 139a, 139b, respectively, in other embodiments these light sources 136, 138 comprise 3, 4, 5, 6, 7, 8, 9, 10 or more light sources.

The blue 136 and white light 138 utilize LEDs as the light source to produce illumination. In other embodiments alternate sources of illumination are utilized such as, other electroluminescent sources, incandescent sources and gas discharge sources. From the teaching herein a skilled person is readily able to select a suitable light source for device 100.

Figure 3A:
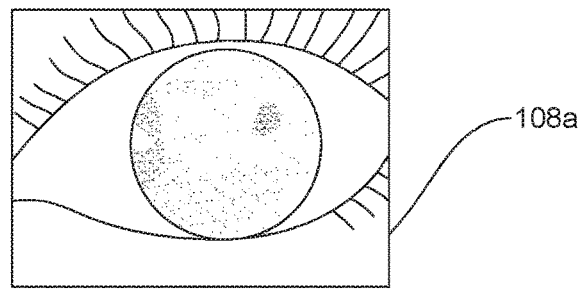
FIG. 3A: is a photograph showing an LED light artefact extending from the lower left to upper right.
Figure 3B:
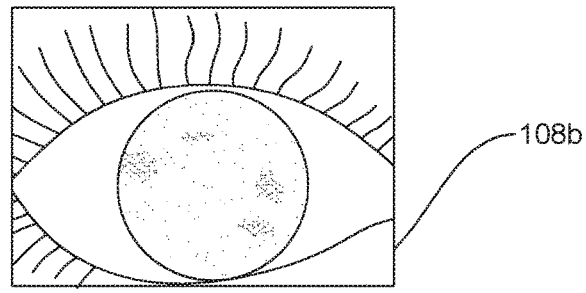
FIG. 3B: is a photograph showing an LED light artefact extending from the upper left to lower right.
Figure 3C:
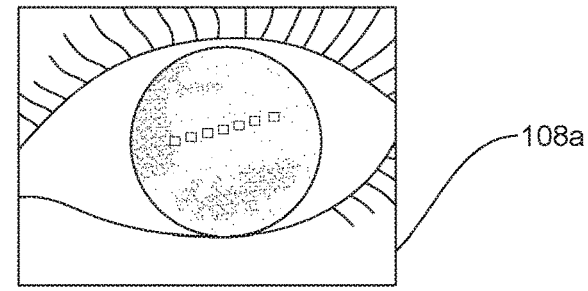
FIG. 3C: is the same photograph shown in FIG. 3A with a line superimposed to illustrate the angle of the LED light artifice.
Figure 3D:
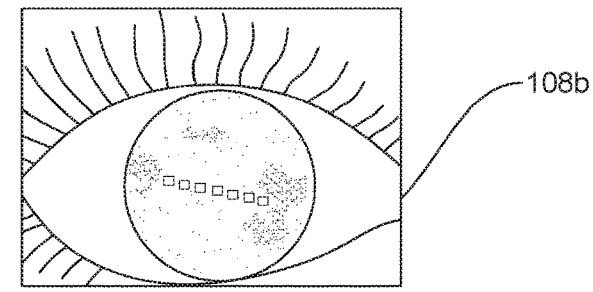
FIG. 3D: is the same photograph shown in FIG. 3B with a line superimposed to illustrate the angle of the LED light artifice.
Figure 4:
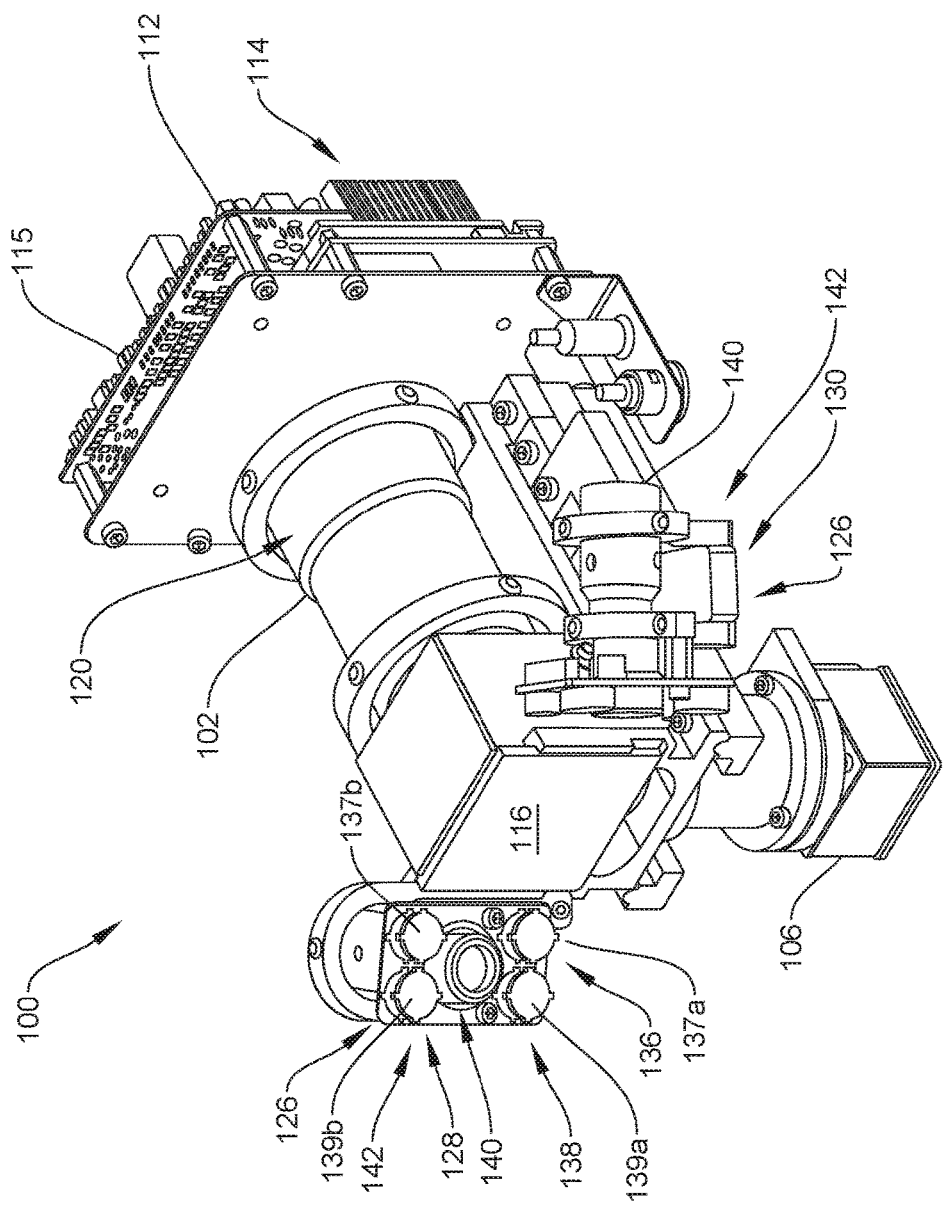
FIG. 4: is a perspective view of a device according to one embodiment of the invention.

Individual LEDs in blue light 136 or white light 138 may be illuminated alternately in a series of captured images so that the LED light artefact occurs at a different location in different images in the series. FIGS. 3A-3D illustrate how the lighting array 126 may be used to direct incident light at a plurality of angles. FIG. 3A shows capture image 108a which has been obtained with a LED light artefact extending from the bottom left to upper right of image 108a (image 108a is of a left eye and the light artefact extends from the bottom right of the imaged left eye to the upper left). On the other hand, FIG. 3B shows capture image 108b which has been obtained with a LED light artefact extending from the upper left to lower right of image 108b (image 108 is of the same left eye and the light artefact extends from the top right of the imaged left eye to the lower left). FIG. 3C shows capture image 108a from FIG. 3A with the sole addition of a dotted line superimposed to show the angle of the light artefact. FIG. 3D shows capture image 108b from FIG. 3A with the sole addition of a dotted line superimposed to show the angle of the light artefact.

The different capture images 108a and 108b were obtained by illuminating different white LEDs on the white light source 138. Capture image 108a was obtained while illuminating lower white LED 139a on the second array 130 and upper white LED 139b on the first array 128. On the other hand, capture image 108b was obtained while illuminating upper white LED 139b on the second array and lower white LED 139a on the first array.

The pairs of light sources illuminated in different members of a series of images that allow elimination of a light artefact may be referred to as complementary pairs. Using the embodiment shown in FIG. 1A, and with reference to the white light only, the complementary pairs comprise lower white LED 139a on the second array 130 and upper white LED 139b on the first array 128 as a first pair; and upper white LED 139b on the second array and lower white LED 139a on the first array as a second pair.

These two pairs may be said to be the complement of the other and therefore, the light source may be said to be complementarily illuminated to provide this set of two images which allow elimination of the light artefact.

The acquisition of capture image 108a and 108b, with the light artefact at different locations on the cornea, allows the area underneath the artefacts to be visualised by looking at both images 108a and 108b which have the artefact over different locations or by constructing a composite image.

The set of images for elimination of the light artefact may comprise two or more images. In one embodiment the set comprises two images. A first image obtained with illumination of the first pair and a second image obtained with illumination of the second pair. In other embodiments, the set comprises 2, 3, 4, 5, 6, 7, 8, 9, 10 or more images.

A similar series of capture images 108a, 108b allowing elimination of the light artefact can be obtained with selective alternate illumination of the complementary pairs of blue LEDs 137a, 137b on first 128 and second arrays 130.

The elimination of the light artefact is of significant advantage because it allows the deduction of any ocular pathology obscured by the artefact which would otherwise have been missed.

The white light source 138 may be used to provide narrow and wide beam light. The blue light source 136 may be used to provide light for fluorescein imaging.

The lighting array 136 may be used to provide low-level LED lighting or high-intensity LED lighting which may be strobed with the image capture device 106. When strobed, light pulses are synchronised with trigger signals from the imaging capture device 106.

Significantly, blue light 136 and white light 138 may be illuminated simultaneously for image capture.

Additionally, the intensity of the illuminated light from any one of the light sources may be varied independently. When the light source comprises an LED, the intensity may be varied by varying the current.

As shown in FIG. 1, device 100 may also comprise a wireless touch panel 153 which displays a preview screen 152 comprising the digital image generated by the image capture device 106. Wireless touch panel 153 is connected to controller 112 by wireless connection 151.

Preview screen 152 may be used to display a live preview of the captured image 108 such that the display on preview screen 152 is the live image being generated by image capture device 106. Preview screen 152 may also be referred to as an electronic viewfinder.

Touch panel 153 may also display a graphical user interface (GUI) that a user may interact with to control device 100.

Touch panel 153 may comprise a touch sensitive transparent screen 154 overlaid on the viewing screen. When the screen is touched a signal is sent to the controller 112. Touch screen may be able to register multiple touch events (such as two or more fingers touching simultaneously) and provide track information for both touch points as the fingers are moved over the touch screen surface.

Wireless touch panel 153 is an Apple iPad tablet computer connected through WiFi, although other types of tablet computer, smart phone or computer and other types of wireless connection may be utilised. In other embodiments preview screen 152 and the GUI may be displayed instead or additionally on a conventional video display comprised in a conventional computer system such as a conventional computer monitor like video display 214 described below. From the teaching herein a skilled person is readily able to select a suitable medium for display of preview screen 152.

In the embodiment shown in FIG. 1, controller 112 comprises an embedded computer 114 comprising a processor 156, circuit board 115, memory 158, networking device 163 and power supply 164. The processor 156 and circuit board 115 are comprised of a EPIA-p900 board and computer 114 also comprises random access memory (RAM) comprising ME-NB-DDR3-1333-4G and operates Windows 7. In other embodiments, controller 114 may comprise other control devices such as, general purpose computer module 201 described below.

In the embodiment shown in FIG. 1A, controller 112 is located in housing 120. In other embodiments controller 120 is located external to housing 120.

Networking device 163 may comprise a network card, modem or other suitable device, which allows controller 112 to connect to a network to communicate with other computing devices.

Processor 156 operates similarly to processor 205 described below to perform the various operations of device 100 and the methods of the invention.

Either processor may process the series of images or the composite image using an algorithm to detect a disease or condition requiring referral and/or treatment. When a disease or condition requiring referral and/or treatment is detected, the device may connect to a remote computer at which the referral and/or treatment may be performed.

Although embedded computer controller 114 is not shown to be connected to any network, apart from the local connection to touch panel 153, similarly to as described with reference to computer module 201, embedded computer controller 114 may also be connected to a network such as, wide area network 220 and/or local computer network 222.

Embedded computer 114 was constructed with the dedicated function of operating device 100. Device 100 may also be operated with other types of controllers 114, including for example, a general purpose computer or general purpose computer system like computer module 201 and system 200 shown in FIGS. 8A and 8B.

Computer system 200 is formed by a controller 114 comprising a general purpose computer module 201 comprising input devices such as a keyboard 202, a mouse pointer device 203, image capture device 106, external hard drive 227 and a microphone 280; and output devices including display device 102, lighting array 126, lenses 124, 132 and lens series 134, video display 214 and loudspeakers 217. Video display 214 is a conventional computer monitor such as, a thin-film transistor LCD (TFT-LCD) panel display which may comprise a touch screen.

A Modulator-Demodulator (Modem) transceiver device 216 may be used by the computer module 201 for communicating to and from a communications network 220 via a connection 221. The network 220 may be a wide-area network (WAN), such as the Internet, a cellular telecommunications network, or a private WAN. Through the WAN 220, computer module 201 may be connected to other similar computer modules 290 and 291. Where the connection 221 is a telephone line, the modem 216 may be a traditional "dial-up" modem. Alternatively, where the connection 221 is a high capacity, for example a cable, connection, the modem 216 may be a broadband modem. A wireless modem may also be used for wireless connection to network 220.

The computer module 201 typically includes at least one processor 205, and a memory 206 for example formed from semiconductor random access memory (RAM) and semiconductor read only memory (ROM). The module 201 also includes a number of input/output (I/O) interfaces including: an audio-video interface 207 that couples to the image display device 102, video display 214, loudspeakers 217 and microphone 280; an I/O interface 213 for the keyboard 202, mouse 203, capture device 106 and external hard drive 227; and an interface 208 for the external modem 216 and lighting array 126, lens 124, lens 132 and lens system 134. In some implementations, modem 216 may be incorporated within the computer module 201, for example within the interface 208. The computer module 201 also has a local network interface 211 which, via a connection 223, permits coupling of the computer system 200 to a local computer network 222, known as a Local Area Network (LAN).

Figure 8A:
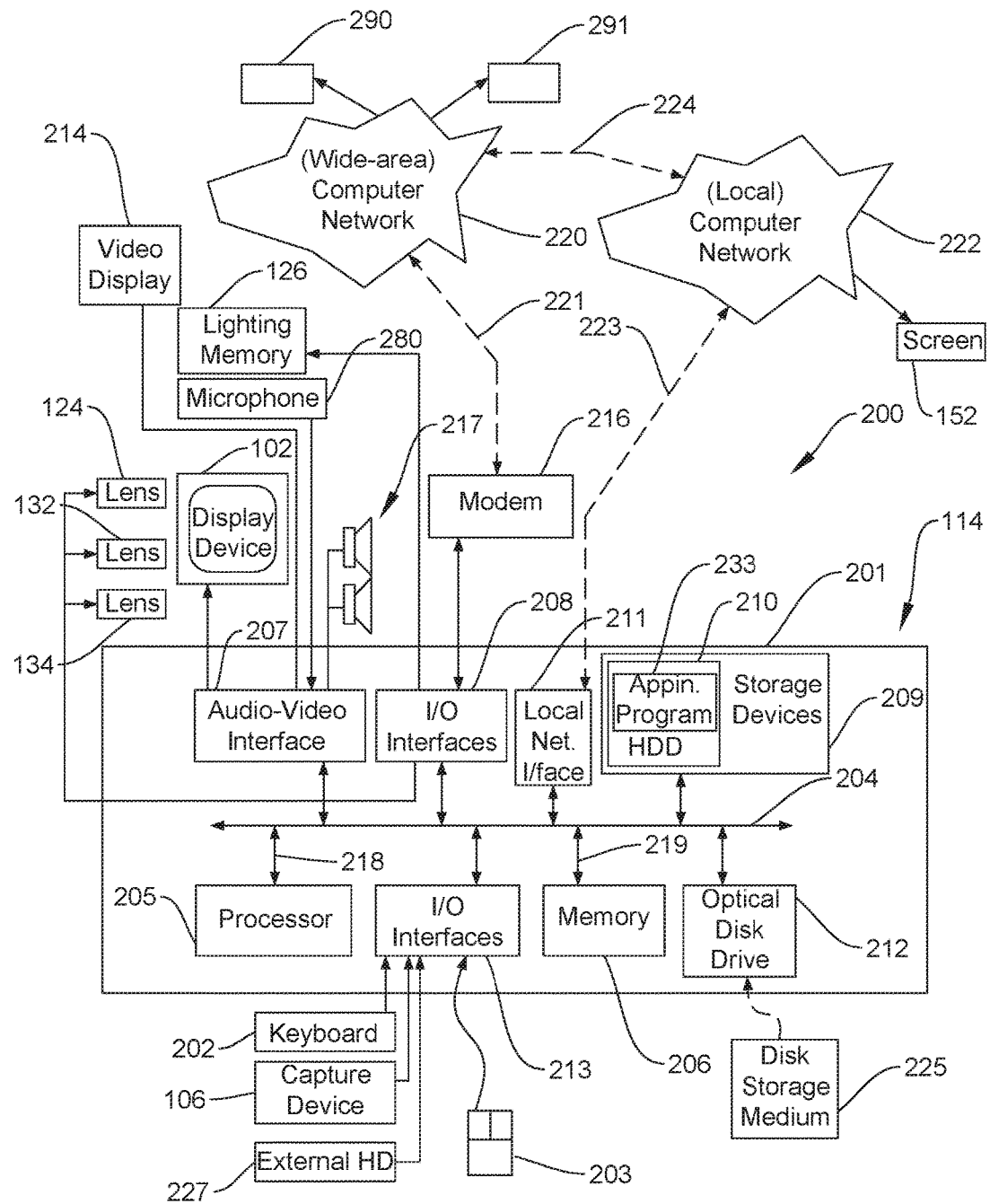
FIG. 8A and FIG. 8B: are schematic diagrams of one embodiment of a general purpose computer suitable for use in one embodiment of the invention.

FIG. 8A also shows that computer module 201 may connect to preview screen 152 through local LAN 222. In other embodiments this connection is via a wireless protocol such as, Bluetooth, Airplay, or other similar local network protocol.

As also illustrated, the local network 222 may also couple to the wide network 220 via a connection 224, which would typically include a so-called "firewall" device or device of similar functionality. The interface 211 may be formed by an Ethernet circuit card, a Bluetooth wireless arrangement or an IEEE 802.11 wireless arrangement or other suitable interface.

The I/O interfaces 208 and 213 may afford either or both of serial and parallel connectivity, the former typically being implemented according to the Universal Serial Bus (USB) standards and having corresponding USB connectors (not illustrated).

Storage devices 209 are provided and typically include a hard disk drive (HDD) 210. Other storage devices such as, an external HD 227, disk drive (not shown) and a magnetic tape drive (not shown) may also be used. An optical disk drive 212 is typically provided to act as a non-volatile source of data. Portable memory devices, such optical disks (e.g.: CD-ROM, DVD, Blu-Ray Disc), USB-RAM, external hard drives and floppy disks for example may be used as appropriate sources of data to the computer module 201.

The components 205 to 213 of the computer module 201 typically communicate via an interconnected bus 204 in a conventional mode of operation of computer system 200. In the embodiment shown in FIGS. 8A and 8B processor 205 is coupled to system bus 204 through connections 218. Similarly, memory 206 and optical disk drive 212 are coupled to the system bus 204 by connections 219. Examples of computers on which the described arrangements can be practiced include IBM-PC's and compatibles, Sun Sparc stations, Apple Mac or like computer system.

The methods of the invention may be implemented using embedded computer system 114 or computer module 201. The steps or processes of the methods of the invention may be implemented as one or more software application program 233 executable with the computer module 114 or 201.

Figure 8B:
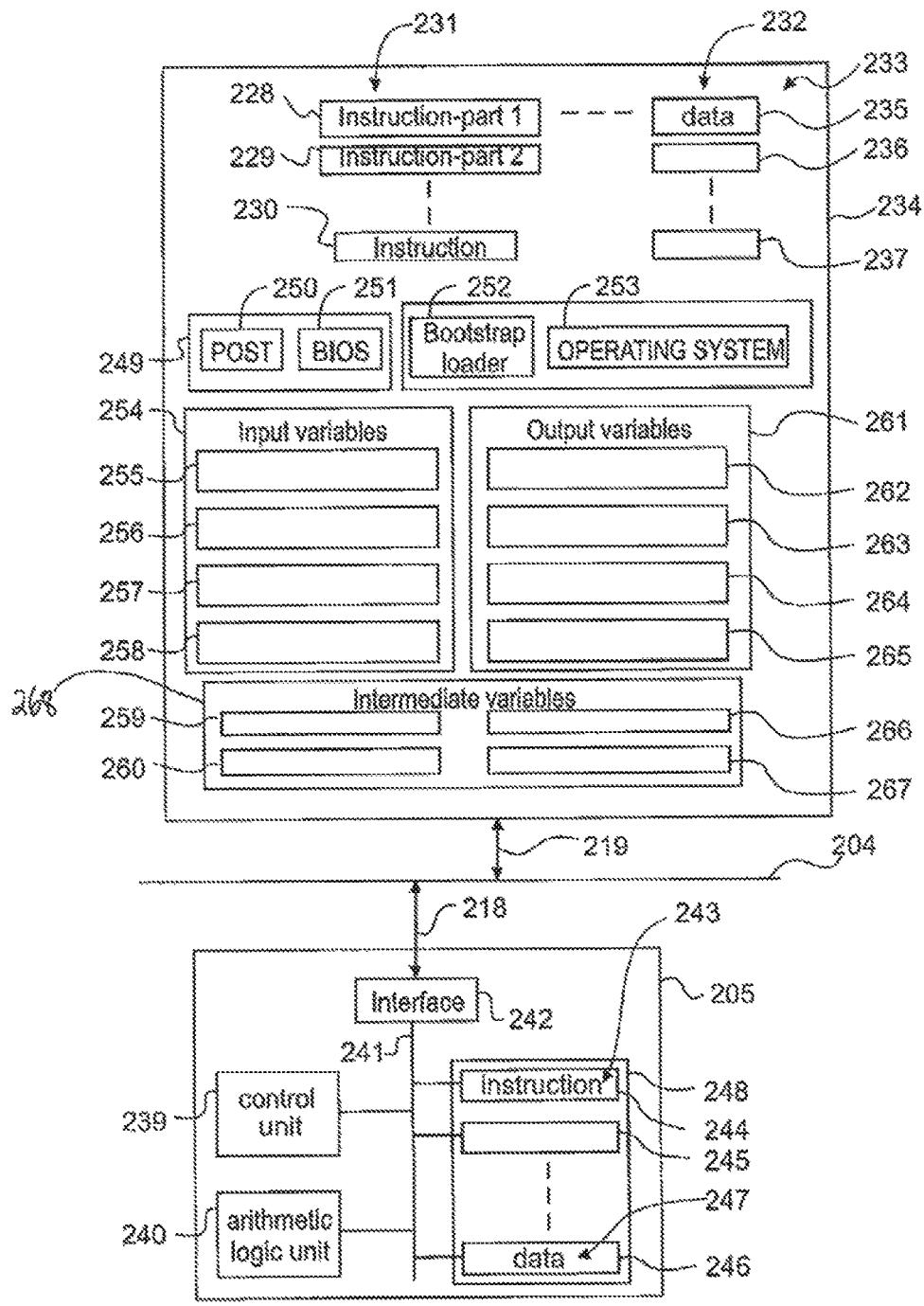

FIG. 8B is a detailed schematic block diagram of the processor 205 and a memory 234. Processor 156 may function in a similar convention manner. The memory 234 represents a logical aggregation of all the memory modules, including the storage device 209 and semiconductor memory 206, which can be accessed by the computer module 201 in FIG. 8A.

The methods of the invention may be implemented using computer system 200 wherein the methods may be implemented as one or more software application programs 233 executable within computer module 201. In particular, the steps of the methods of the invention may be effected by instructions 231 in the software carried out within the computer module 201.

The software instructions 231 may be formed as one or more code modules, each for performing one or more particular tasks. The software may also be divided into two separate parts, in which a first part and the corresponding code modules performs the methods of the invention and a second part and the corresponding code modules manage a GUI between the first part and a user.

The software may be stored in a computer readable medium, including in a storage device of a type described herein. The software is loaded into the computer system 200 from the computer readable medium, and then executed by the computer system 200. A computer readable medium having such software or computer program recorded on it is a computer program product. The use of the computer program product in the computer system 200 preferably affects an advantageous apparatus for implementing the methods of the invention.

The software 233 is typically stored in the HDD 210 and/or the memory 206. The software is loaded into the computer system 200 from a computer readable medium, and then executed by the computer module 201. Thus for example the software 233 may be stored on storage medium 225 that is read by optical disk drive 212. The use of the computer program product in the computer module 201 or system 200 preferably effects an advantageous apparatus for implementing the methods of the invention.

In some instances, the application programs 233 may be supplied to the user encoded on one or more disk storage medium 225, such as a CD-ROM, DVD or Blu-ray Disc, and read via the corresponding drive 212, or alternatively may be read by the user from the networks 220 or 222. Still further, the software can also be loaded into the computer system 200 from other computer readable media. Computer readable storage media refers to any non-transitory tangible storage medium that provides recorded instructions and/or data to the computer module 201 or system 200 for execution and/or processing. Examples of such storage media include floppy disks, magnetic tape, CD-ROM, DVD, Blu-ray Disc, a hard disk drive, a ROM or integrated circuit, USB memory, a magneto-optical disk, or a computer readable card such as a PCMCIA card and the like, whether or not such devices are internal or external of the computer module 201. Examples of transitory or non-tangible computer readable transmission media that may also participate in the provision of software, application programs, instructions and/or data to the computer module 201 include radio or infra-red transmission channels as well as a network connection to another computer or networked device, and the Internet or an Intranet including email transmissions and information recorded on websites and the like.

The second part of the application programs 233 and the corresponding code modules mentioned above may be executed to implement one or more GUIs to be rendered or otherwise represented upon touch panel 153 and/or display 214 or to implement the presentation of displayed image 104. Through manipulation of, typically, keyboard 202, mouse 203, screen 152 and/or screen 214, a user of computer system 200 and the methods of the invention may manipulate the interface in a functionally adaptable manner to provide controlling commands and/or input to the applications associated with the GUI(s). Other forms of functionally adaptable user interfaces may also be implemented, such as an audio interface utilizing speech prompts output via loudspeakers 217 and user voice commands input via microphone 280. The speech prompts and/or user voice commands may be transmitted via network 220 or 222.

When the computer module 201 is initially powered up, a power-on self-test (POST) program 250 executes. The POST program 250 is typically stored in a ROM 249 of the semiconductor memory 206. A hardware device such as the ROM 249 is sometimes referred to as firmware. The POST program 250 examines hardware within the computer module 201 to ensure proper functioning, and typically checks processor 205, memory 234 (209, 206), and a basic input-output systems software (BIOS) module 251, also typically stored in ROM 249, for correct operation. Once the POST program 250 has run successfully, BIOS 251 activates hard disk drive 210. Activation of hard disk drive 210 causes a bootstrap loader program 252 that is resident on hard disk drive 210 to execute via processor 205. This loads an operating system 253 into RAM memory 206, upon which operating system 253 commences operation. Operating system 253 is a system level application, executable by processor 205, to fulfill various high level functions, including processor management, memory management, device management, storage management, software application interface, and generic user interface.

Operating system 253 manages memory 234 (209, 206) in order to ensure that each process or application running on computer module 201 has sufficient memory in which to execute without colliding with memory allocated to another process. Furthermore, the different types of memory available in the system 200 must be used properly so that each process can run effectively. Accordingly, the aggregated memory 234 is not intended to illustrate how particular segments of memory are allocated, but rather to provide a general view of the memory accessible by computer module 201 and how such is used.

Processor 205 includes a number of functional modules including a control unit 239, an arithmetic logic unit (ALU) 240, and a local or internal memory 248, sometimes called a cache memory. The cache memory 248 typically includes a number of storage registers 244, 245, 246 in a register section. One or more internal busses 241 functionally interconnect these functional modules. The processor 205 typically also has one or more interfaces 242 for communicating with external devices via the system bus 204, using a connection 218. The memory 234 is connected to the bus 204 by connection 219.

Application program 233 includes a sequence of instructions 231 that may include conditional branch and loop instructions. Program 233 may also include data 232 which is used in execution of the program 233. The instructions 231 and the data 232 are stored in memory locations 228, 229, 230 and 235, 236, 237, respectively. Depending upon the relative size of the instructions 231 and the memory locations 228-230, a particular instruction may be stored in a single memory location as depicted by the instruction shown in the memory location 230. Alternately, an instruction may be segmented into a number of parts each of which is stored in a separate memory location, as depicted by the instruction segments shown in the memory locations 228 and 229.

In general, processor 205 is given a set of instructions 243 which are executed therein. The processor 205 then waits for a subsequent input, to which processor 205 reacts by executing another set of instructions. Each input may be provided from one or more of a number of sources, including data generated by one or more of the input devices 202, 106, data received from an external source across one of the networks 220, 222, data retrieved from one of the storage devices 206, 209 or data retrieved from a storage medium 225 inserted into the corresponding reader 212. The execution of a set of the instructions may in some cases result in output of data. Execution may also involve storing data or variables to the memory 234.

The disclosed arrangements use input variables 254 that are stored in the memory 234 in corresponding memory locations 255, 256, 257, 258. The described arrangements produce output variables 261 that are stored in the memory 234 in corresponding memory locations 262, 263, 264, 265. Intermediate variables 268 may be stored in memory locations 259, 260, 266 and 267.

The register section 244, 245, 246, the arithmetic logic unit (ALU) 240, and the control unit 239 of the processor 205 work together to perform sequences of micro-operations needed to perform "fetch, decode, and execute" cycles for every instruction in the instruction set making up the program 233. Each fetch, decode, and execute cycle comprises:

(a) a fetch operation, which fetches or reads an instruction 231 from memory location 228, 229, 230;
(b) a decode operation in which control unit 239 determines which instruction has been fetched; and
(c) an execute operation in which the control unit 239 and/or the ALU 240 execute the instruction.

Thereafter, a further fetch, decode, and execute cycle for the next instruction may be executed. Similarly, a store cycle may be performed by which the control unit 239 stores or writes a value to a memory location 232.

Each step or sub-process in the methods of the invention may be associated with one or more segments of the program 233, and may be performed by register section 244-247, the ALU 240, and the control unit 239 in the processor 205 working together to perform the fetch, decode, and execute cycles for every instruction in the instruction set for the noted segments of program 233.

The methods of the invention may alternatively be implemented in dedicated hardware such as one or more integrated circuits performing the functions or sub functions of the described methods. Such dedicated hardware may include graphic processors, digital signal processors, or one or more microprocessors and associated memories.

The device 100 may also comprise a hard switch to select a desired operator interface (operating system) among two or more interfaces that are provided for portability across different computer systems.

Controller 112 may perform operations including: image capture device 106 control and capture; degree and type of lighting by lighting array 126; image processing; an auto-focus algorithm; network connectivity including wireless; data encryption and decryption; visual function testing stimuli presentation and change; error handling; remote system diagnostics and event logging; and automated billing system.

Controller 112 may be used to control image capture device 106 to obtain one or more captured images 108 comprising stereoscopic images of the retina of eye 192; anterior segment images of eye 192; and/or posterior segment images of eye 192. The one or more captured images 108 may be a high resolution colour images. In one embodiment the one or more capture images 108 may be a HDR image. The HDR image may be a composite of 2, 3, 4, 5, 6, 7, 8, 9, 10 or more captured images 108.

Controller 112 is also used to control the illumination of lighting array including the composite components comprising the blue light source 136, blue LEDs 137a, 137b, white light source 138, white LEDs 139a, 139b and slit light source 140. This controlled lighting may achieve illumination by white flood light, narrow slit light and blue light and also to produce a series of captured images 108 comprising different types of illumination such as to allow elimination of the light artefact for example, image series 108a and 108b.

Controller 112 may process the captured image 108 using any image processing technique.

Controller 112 may also be used to control lenses 124, 132, 134. For example, processor 156 may change the focus of display lens 132 to achieve the infinity focus detailed above. Processor 156 may also be used to change the focus of objective lens 124 to project the eye 192 to infinity when imaging the anterior segment of eye 192.

Controller 112 may also be used to store the captured images in memory 158. Memory 158 may also store any input or obtained patient data, operator data or a part thereof.

Controller 112 may be used to optimise the image capture device 106, to optimise illumination by lighting array 126 and to optimise performance of lenses 126, 132, 134. Controller 112 is also used to control image display device 102 to select and change displayed image 104.

Controller 112 may be Web 2.0 compliant and may comprise a machine IP address.

As shown in FIG. 8A, controller 112 may be connected to a network so that one or more captured images 108, patient data and/or operator data may be transmitted to a remote site.

Figure 9:
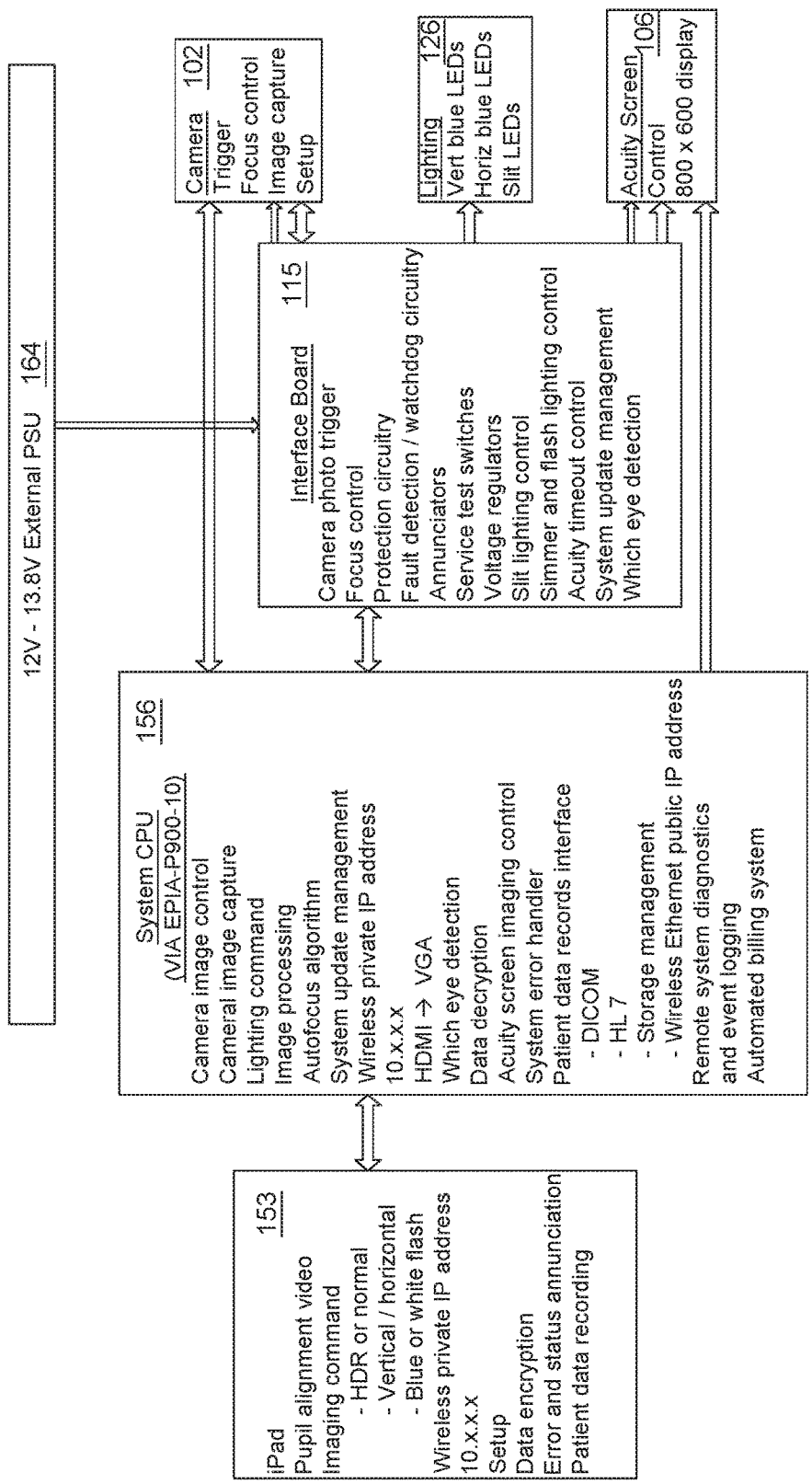
FIG. 9: is a block diagram summarising the electronic components in one embodiment of the invention.

FIG. 9 shows a system block diagram summarizing the electronic components and their functions in one embodiment of device 100.

Device 100 may also obtain and/or store patient data 160. Part or all of the patient data 160 may be input by the patient or other user using screen 152 or another similar or identical screen 152 or using one of the inputs to computer module 201, i.e. such as keyboard 202, mouse 203, display 214 and microphone 280. Patient data 160 that is input into device 100 may be referred to as input patient data 160a. In another embodiment part or all of the patient data 160 may be obtained from a remote computer or server such as computers 290, 291 through a network like network 220. Patient data that is obtained may be referred to as obtained patient data 160b. Part or all of the patient data, regardless of location or transmission status may be encrypted.

Input patient data 160a may comprise demographic and related health data input via the GUI.

A user operating device 100 may also input operator details 161, such as, their name, location and identifying number using an input such as, screen 152 or another similar or identical screen 152 or using an input connected to computer module 201. Part or all of the operator details, regardless of location or transmission status may be encrypted.

The user or patient 190 may also input a response to the displayed image 104 as eye test response data 162. The eye test response data 162 may comprise information such as the smallest letter/number/picture able to be read on a Snellen chart; lowest row on a Landolt C Chart; response to Amsler Grid Test normal or perception of missing, bent or distorted looking areas. The eye test response data may be input into an input such as, screen 152, mouse 203, display 214, microphone 280 or keyboard 202. Part or all of the eye test response data 162, regardless of location or transmission status may be encrypted.

The patient data 160, operator details 161, eye test response data 162 may be stored for a short or long term on device 100 in one or more of memory 158, 206 or 209.

When encrypted data is sent to a remote computer such as, computers 290, 291, software on the remote computer will comprise a decryption algorithm.

The data obtained and/or stored in device 100 may be referred to as ophthalmic screening data 165. The ophthalmic screening data 165 may comprise one or more captured image 108, optionally, along with one or more of patient data 160, operator details 161 and eye test response data 162.

Controller 112 may also comprise software which collates ophthalmic screening data 165 and transmits data 165 to a remote location via a network.

Using network 220, ophthalmic screening 165 data may be transmitted to a remote computer, such as, computer 290, 291. The remote computers may be located at a tertiary ophthalmic service or at another location where an ophthalmologist or other person with specialist training may review the screening data 165 to determine a course of action. The course of action may be no further treatment required, scheduling of an appointment or transfer to a tertiary treatment centre. The course of action may be communicated via network 220 to controller 114 for display on display 214 or 153.

Device 100 may comprise a slit-lamp biomicroscope function.

Figure 10:
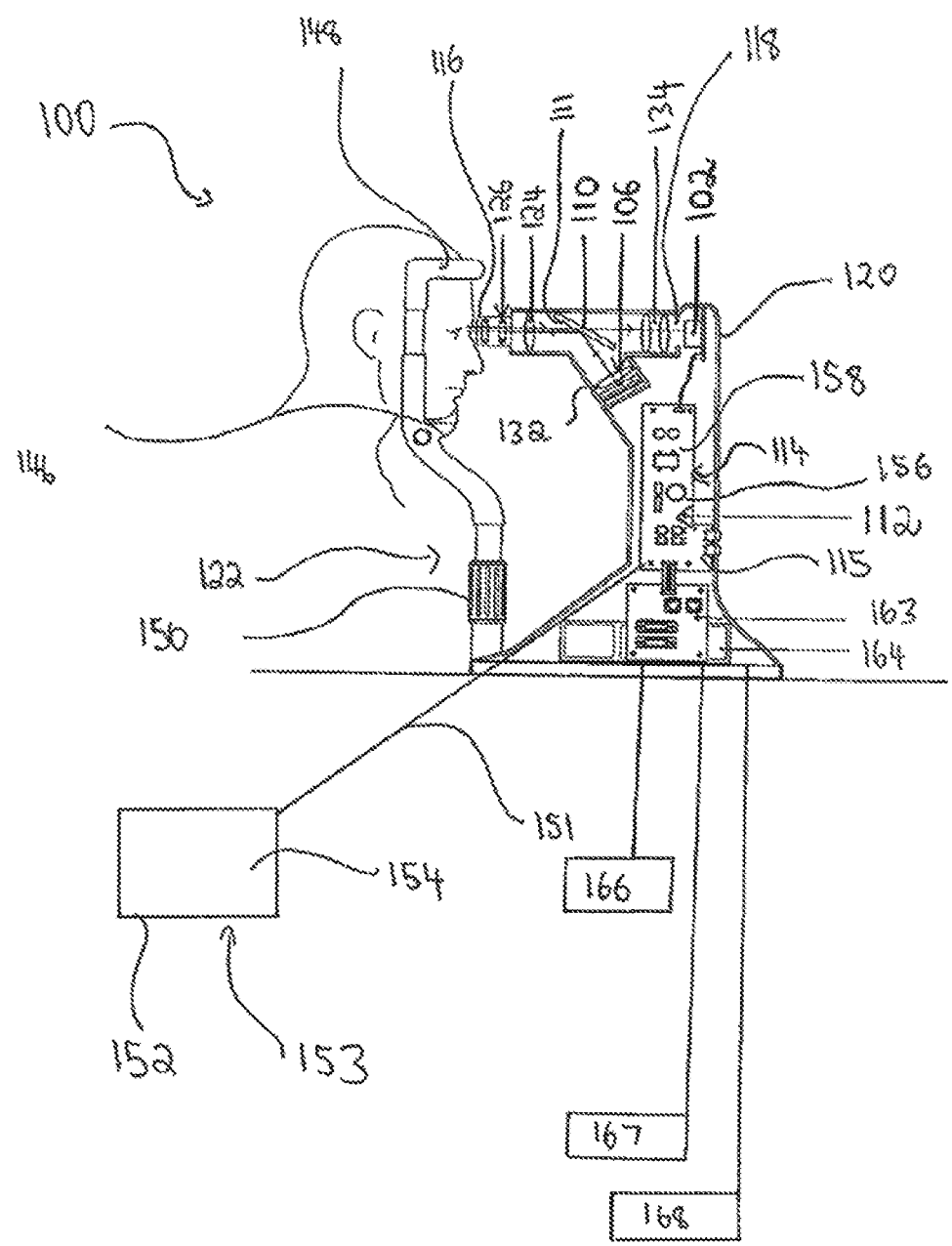
FIG. 10: shows another embodiment of a device according to the invention.

Device 100 may also comprise one or more additional ophthalmological tool such as, a perimeter, a retinal camera and/or a retinal screening tool. FIG. 10 shows an embodiment of device 100 in which perimeter 166, a retinal camera 167 and a retinal screening tool 168 are connected to device 100 and may be controlled by controller 114 using the GUI. The perimeter 166, retinal camera 167 and retinal screening tool 168 may also be connected to computer module 201 through one of I/O interfaces 208, 213 or through an additional I/O interface.

Device 100 may also comprise a laser treatment device 169 that may be connected to and controlled by controller 114 using the GUI. The laser treatment device 169 may also be controlled by a user located remotely using a networked computer such as, computers 290, 291.

Figure 11A:
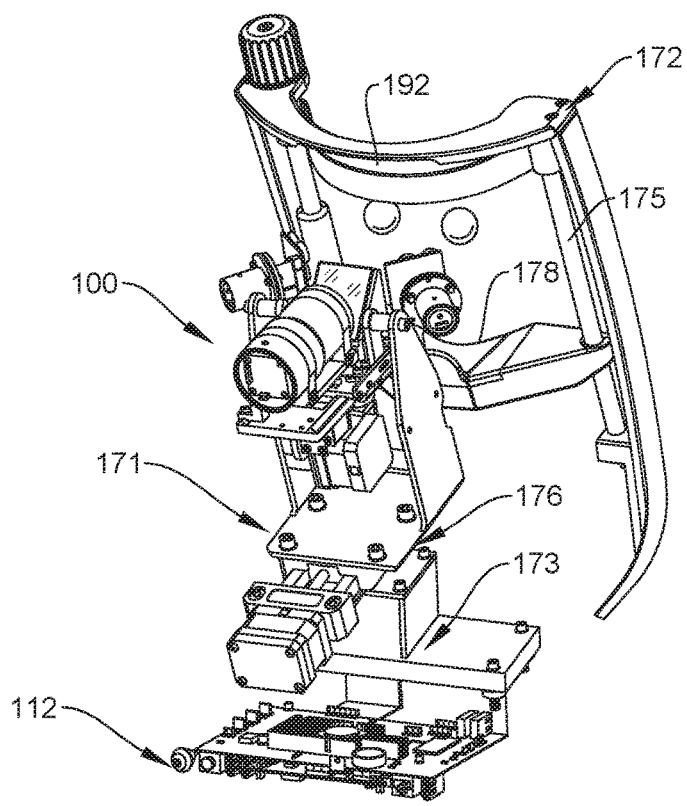
FIG. 11A and FIG. 11B: show one embodiment of a positioning device according to the invention.
Figure 11B:
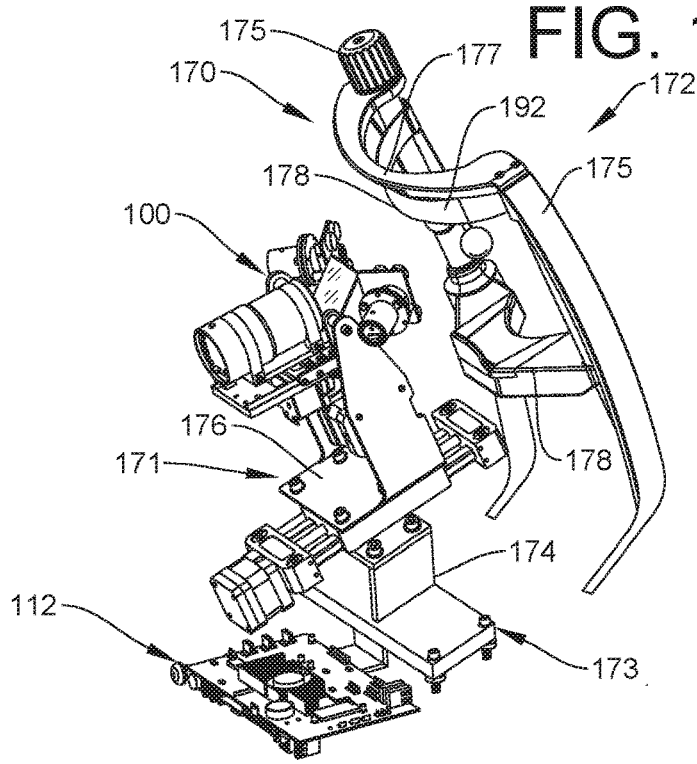

FIGS. 11A and 11B show views from different angles of another positioning device 170 which may be used with the device 100 and methods of the invention in place of positioning device 122. Positioning device 170 comprises a body 171 comprising a head receiving section 172, base 173, x-axis adjustment arm 174, y-axis adjustment arm 175 and z-axis adjustment arm 176. The head receiving section 172 comprises a forehead rest 177 and a chin rest 178.

X-axis adjustment arm 174 allows both fine adjustment to centre the eye 192 in the field of view of image capture device 102 and coarse adjustment to swap from one eye to the other eye.

Y-axis adjustment arm 175 allows fine up and down adjustment to centre eye 192 in the field of view of image capture device 102.

Z-axis adjustment arm 176 allows movement to effect coarse focus adjustment. Image capture device 102 provides the fine focus.

The focus adjustment may be aided by substitution of chin rest 170 with a dual chin rest 180 (not shown). Coarse adjustment can then be completed by the patient moving their chin from one chin rest to the other and fine adjustment may be done by x-axes adjustment arm.

Although not shown, in other embodiments positioning device 170 may comprise a motor to drive movement along one or more axes. In these motorized embodiments, positioning device 170 may automatically centre device 100 over eye 192 in response to an auto-focus algorithm or a command such as, a user touch on the centre of eye as displayed on touch panel 153.

The autofocus algorithm may be implemented by controller 112 directing movement of positioning device 170. The auto-focus algorithm may select and locate a region of interest in displayed image 104 and use an algorithm to focus on eye 192. The region of interest may comprise one or more of: eyelash(es); eyelids; cornea or iris.

In the embodiment shown in FIGS. 11A and 11B, positioning device 170 is set at an angle comprising 20 degrees to assist the patient head position in head receiving section 172. In other embodiments, the angle may comprise 5 to 35 degrees; 10 to 30 degrees; or 15 to 25 degrees. The angle may comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 degrees. In the embodiment shown, this angling is achieved by orienting x-axis adjustment arm 175 away from vertical.

Although the invention has been described with reference to eye 192, it is understood that both patient eyes may be examined one at a time.

Significantly, the present invention allows the integration of vision testing functions in one ready-to-use platform. The present invention is also of great advantage because of its simplicity of use at both the user and remote ends. This simplicity gives the capacity to capture good quality images with minimal complexity and with little training. The invention also allows high speed relay with minimal delay through standard telemedicine and network portals along with the transfer between distant sites of patient medical records, medical images and output data from medical devices.

Another advantage of the invention is that device 100 has a comparatively low cost and small foot print and weight compared to other instruments.

The present invention is the first integrated tele-ophthalmic system which provides anterior and posterior image capture, vision testing and encrypted patient data storage and transmission.

The invention claimed is:

1. An eye testing and image capture device for testing and examination of an eye comprising:
    an image display device to display an image for viewing by an eye to be tested;
    an image capture device to capture an image of the eye to be examined;
    a beam splitter positioned to split light between the image capture device and the image display device; and
    a lighting array for illuminating the eye to be tested and imaged wherein the lighting array comprises a first array positioned at a first angle to the eye and a second array positioned at a second angle to the eye, the second angle being different from the first angle, and the first array and second array comprise two or more different light types,
    wherein the first array is arranged in a first lighting housing and the second array is arranged in a second lighting housing, the second lighting housing different from the first lighting housing.

2. The device of claim 1 wherein the displayed image is viewed by or visible to the eye simultaneously with the captured image being captured.

3. The device of claim 1 wherein the two or more light types comprise white light and light of a defined wavelength.

4. The device of claim 3 wherein the light of a defined wavelength comprises coloured light.

5. The device of claim 1 wherein the two or more light types comprise a slit light source.

6. The device of claim 1 wherein the light types comprise a blue light source, a white light source and a slit light source.

7. The device of claim 1 wherein each of the two or more different light types comprises respective lower light sources and upper light sources which may be individually complementarily illuminated in a series of captured images so that a light artefact may be eliminated or at least substantially reduced.

8. The device of claim 7 further comprising an image processor to process the series of images to produce a composite image with elimination or substantial elimination of the light artefact and to process the series of images or the composite image using an algorithm to detect a disease or condition requiring referral and/or treatment.

9. The device of claim 8 wherein when a disease or condition requiring referral and/or treatment is detected, the device connects to a remote computer at which the referral and/or treatment is performed.

10. The device of claim 1 wherein the device is connected to a network for communication of ophthalmic screening data to a remote location and optionally for receiving a determination based on a review of the ophthalmic screening data at the remote location.

11. A system for screening a patient, the system comprising:

an input into which eye test response data and optionally operator details and/or patient data is entered, the input comprising eye test information;

the image capture device of claim 1 to capture one or more image of an eye of the patient, the captured one or more image comprising eye image information;

a computer for providing the obtained eye test information and eye image information to a remote computer via a network;

the remote computer for reviewing the obtained eye test information and eye image information at a location remote to the computer and for entering a determination of a next course of action based on the review;

receiving on the computer the determined next course of action through the network.

12. A method of obtaining eye test data and one or more image of an eye, the method comprising:

illuminating the eye to be tested and imaged with an illumination device comprising a first lighting array positioned at a first angle to the eye and a second lighting array positioned at a second angle to the eye, the second angle being different from the first angle, wherein the first lighting array and second lighting array comprise two or more different light types, wherein the first lighting array is arranged in a first lighting housing and the second lighting array is arranged in a second lighting housing, the second lighting housing different from the first lighting housing;

displaying an image for viewing by the eye on an image display device;

capturing an image of the eye with an image capture device; and splitting light between the image capture device and the image display device wherein the displayed image is viewed by the eye simultaneously with the captured image being captured.

13. The method of claim 12 wherein the two or more light types comprise white light and light of a defined wavelength.

14. The method of claim 13 wherein the light of a defined wavelength comprises blue light.

15. The method of claim 12 wherein the two or more light types further comprise a slit light source.

16. The method of claim 12 wherein the light types comprise a blue light source, a white light source and a slit light source.

17. The method of claim 12 wherein each of the two or more different light types comprise respective lower light sources and upper light sources and the method further comprises individually complementarily illuminating the respective lower light sources and upper light sources in a series of captured images so that a light artefact is eliminated or at least substantially reduced.

18. The method of claim 17 wherein the method further comprises processing the series of images with an image processor to produce a composite image with elimination or substantial elimination of the light artefact and processing the series of images or the composite image using an algorithm to detect a disease or condition requiring referral and/or treatment.

19. The method of claim 12 wherein the method further comprises communicating ophthalmic screening data to a remote location via a network and optionally receiving a determination based on review of the ophthalmic screening data at the remote location via the network.

20. A method for screening a patient, the method comprising:

inputting eye test response data and optionally operator details and/or patient data into a computer, the input data comprising eye test information;

the capturing with the method of claim 12 one or more image of an eye of the patient the captured one or more image comprising eye image information;

providing with a computer the obtained eye test information and eye image information to a remote computer via a network;

displaying on a remote computer the obtained eye test information and eye image information at a location remote to the computer for review;

entering a determination of a next course of action based on the review into the remote computer; and receiving on the computer the determined next course of action through the network.

* * * * *